(12) United States Patent
Atrazhev

(10) Patent No.: US 8,986,959 B2
(45) Date of Patent: Mar. 24, 2015

(54) SETTING OF MULTIPLE PRIMING OLIGONUCLEOTIDES FOR SOLID GEL AMPLIFICATION IN HYDROGELS

(75) Inventor: Alexey Atrazhev, Edmonton, CA (US)

(73) Assignee: The Governors of the University of Alberta, Edmonton, Alberta (CA)

( * ) Notice: Subject to any disclaimer, the term of this patent is extended or adjusted under 35 U.S.C. 154(b) by 0 days.

(21) Appl. No.: 13/819,420

(22) PCT Filed: Aug. 29, 2011

(86) PCT No.: PCT/CA2011/000989
§ 371 (c)(1),
(2), (4) Date: Feb. 27, 2013

(87) PCT Pub. No.: WO2012/027832
PCT Pub. Date: Mar. 8, 2012

(65) Prior Publication Data
US 2013/0157278 A1    Jun. 20, 2013

Related U.S. Application Data

(60) Provisional application No. 61/378,082, filed on Aug. 30, 2010.

(51) Int. Cl.
*C12P 19/34* (2006.01)
*C12Q 1/68* (2006.01)

(52) U.S. Cl.
CPC ............. *C12Q 1/686* (2013.01); *C12Q 1/6844* (2013.01); *C12Q 2565/501* (2013.01); *C12Q 2565/518* (2013.01); *C12Q 2565/629* (2013.01)
USPC ........................... 435/91.2; 435/6.1; 435/6.12

(58) Field of Classification Search
USPC .......................................... 435/6.1, 6.12, 91.2
See application file for complete search history.

(56) References Cited

U.S. PATENT DOCUMENTS

| | | | |
|---|---|---|---|
| 5,616,478 A | 4/1997 | Chetverin et al. | |
| 6,514,768 B1 * | 2/2003 | Guire et al. ................... | 436/518 |
| 2003/0166263 A1 * | 9/2003 | Haushalter et al. ........ | 435/287.2 |
| 2006/0110722 A1 | 5/2006 | Beebe et al. | |
| 2009/0105082 A1 | 4/2009 | Chetverin et al. | |

FOREIGN PATENT DOCUMENTS

| | | |
|---|---|---|
| WO | 2007111639 | 10/2007 |
| WO | 2012003579 | 1/2012 |

OTHER PUBLICATIONS

Mitra et al: In Situ Localized Amplification and Contact Replication of Many Individual DNA Molecules; Nucleic Acids Research, 1999, vol. 27, No. 24, e34; p. 1-6.
Strizhkov et al.: PCR Amplification on a Microarray of Gel-Immobilized Oligonucleotides: Detection of Bacterial Toxin- and Drug-Resistant Genes and Their Mutations; Bio Techniques; 29; vol. 29, No. 4(2000); p. 844-857.

* cited by examiner

*Primary Examiner* — Ardin Marschel
(74) *Attorney, Agent, or Firm* — Anthony R. Lambert

(57) ABSTRACT

The present invention provides for a novel system and method for amplification and detection of nucleic acids within a microfluidic device wherein multiple nucleotides capable of priming PCR are present within the system and substantially sequestered within separate hydrogel posts therein.

3 Claims, 11 Drawing Sheets

(a)            (b)

(a)

(b)

(c)

(a)

(b)

(c)

(a)

(b)

(c)

(d)

(a)

(b)

(c)

(d)

SETTING OF MULTIPLE PRIMING OLIGONUCLEOTIDES FOR SOLID GEL AMPLIFICATION IN HYDROGELS

CROSS-REFERENCE TO RELATED APPLICATIONS

The present application claims priority from U.S. provisional patent application No. 61/378,082 filed Aug. 30, 2011, such application is expressly incorporated by reference herein for all purposes.

CROSS-REFERENCE TO SEQUENCE LISTING

This application hereby incorporates by reference in its entirety an amended Sequence Listing which has been submitted via EFS-Web in ASCII format as a file entitled "72109_SEQUENCE_LISTING_amended.txt", created on Mar. 27, 2013, which has a file size of 2.26 KB.

FIELD OF THE INVENTION

The present invention pertains to the field of macro- and microfluidic devices and methods for detection of nucleic acids

BACKGROUND OF THE INVENTION

All of the publications, patents and patent applications cited within this application are herein incorporated by reference in their entirety to the same extent as if the disclosure of each individual publication, patent application or patent was specifically and individually indicated to be incorporated by reference in its entirety.

There is an increasing demand for a small scale array-based and/or microfluidic device that processes micro- or nano-volumes of sample, with time and cost savings arising from miniaturization. Prior art approaches to miniaturised polymerized chain reactions ("PCR") make use of open or enclosed chambers or flow through zones/channel networks with appropriate temperature regulation; some have on-board silicone rubber-based or magnetic-based valving and/or pumping. Although potentially powerful approaches, challenges may arise of pressure seal and/or evaporation, pressure buffering, as well as others such as chemical interference through surface interactions, and evaporation/contamination via the porous, gas permeable membranes used in pumps and valves.

Performing PCR in a colloidal hydrogel matrix (hereafter termed "gel") may confer a multitude of advantages. For example, the DNA, polymerase enzyme and other PCR reagents a) have reduced access to the device materials' surfaces where they may be adsorbed, absorbed, poisoned or otherwise rendered inactive and b) are kept within close proximity to each other without the need for valves or pumps. Likewise, any contaminant solutes from device materials have reduced access to the PCR reaction.

Gels provide a successful medium for PCR, as first introduced by Chetverin et al., see for example U.S. Pat. No. 5,616,478; which is herein incorporated by reference in its entirety. PCR was confined to circular spots in a gel sheet where the initial DNA or RNA templates, formed "molecular polonies' (short for polymerase colonies), named for their similarity to the growth of bacterial colonies in agar; the initial amount of DNA can be accurately estimated by counting the number of polonies. Mitra et al. (Mitra, R. D. et al; *Nucleic Acid Research* 1999, 27, e34) performed DNA amplification in a thin acrylamide film polymerized with all the reagents along with plasmid DNA as their template. In an alternate approach, Strizhkov et al. (Strizhkov, B. N. Et al; *Biotechniques* 2000, 29, 844-848) used nanoliter gel pads to immobilize primers for PCR. Single Nucleotide Polymorphisms (SNPs) in cDNA were detected with polony technology by Butz et al. (Butz, J. et al, BMC Biotechnol 2003, 3:11)

Absent the use of immobilized primers within the gel, previous instances of in-gel PCRs were performed in a defined chamber with relatively large volumes (62-65 μL). The present art is in need of a means to perform seamless post PCR analysis of amplicons, such as melting curve analysis ("MCA").

SUMMARY OF THE INVENTION

The present art has suffered from an inability to perform seamless PCR and MCA within an array of defined spaces of microfluidic volumes absent the immobilizing of at least one of the primers involved in the PCR. Further, the art is in need of establishing differing primer combinations within the post elements forming the post array.

In one aspect, the present invention provides for a method for detecting a nucleic acid molecule, including DNA, cDNA or RNA, within a hydrogel post array comprising providing a hydrogel post array of 2×1 or greater containing a cell-free, enzymatic, nucleic-acid amplification system; distributing on at least one of said hydrogel posts nucleic acid molecules, at least one of which may comprise a template for said amplification system; and incubating said hydrogel posts under conditions promoting the synthesis of an amplified nucleic acid product by said amplification system from said at least one template; wherein said amplification system comprises at least two non-immobilized nucleic acids capable of promoting synthesis of amplified nucleic acid product from said template and wherein the posts within the hydrogel post array contains at least two different combinations of at least two non-immobilized nucleic acids capable of promoting synthesis of amplified nucleic acid products from said template.

In a further aspect, the hydrogel posts contain a fluorescent marker, wherein said fluorescent marker has different fluorescence properties when interacting with double-stranded nucleic acids than with single-stranded nucleic acids and in a still further aspect said fluorescent marker is LC Green or SYBR Green. In another aspect, PCR products can be detected by any agent or characteristic that has a different measurable property with one form of nucleic acid than another.

In another aspect, the hydrogel post is comprised of cross-linked polyacrylamide of 2.2%-3.1% weight per unit volume, and photo-polymerized in the absence of APS. In another aspect the polyacrylamide is 3.1%-12% weight per volume. In another aspect the template is included in said hydrogel posts. In another aspect the template is provided externally to said hydrogel posts.

In another aspect the present invention provides for a method for detecting a nucleic acid molecule within a hydrogel post array comprising
  a) Depositing on a substantially planar surface at least one aqueous solution containing at least one nucleic acid capable of priming PCR and a polymeric viscosity increasing solute, said at least one aqueous solutions not being in fluid communication with each other and;
  b) Allowing said aqueous solution to evaporate forming a multiplicity of deposits;
  c) Establishing a hydrogel post array of 2×1 or greater containing a cell-free, enzymatic, nucleic-acid amplification system, said hydrogel posts comprising the array are arranged such that each hydrogel post within the array impinges on only one deposit.

d) distributing on at least one of said hydrogel posts nucleic acid molecules which may contain a nucleic acid capable of acting as a template for said amplification system;

e) incubating said hydrogel posts under conditions promoting the synthesis of an amplified nucleic acid product by said amplification system;

wherein the posts within the hydrogel post array contain at least two different combinations of at least two non-immobilized nucleic acids capable of promoting synthesis of amplified nucleic acid products from said template.

The accompanying description illustrates preferred embodiments of the present invention and serves to explain the principles of the present invention

DETAILED DESCRIPTION OF THE PRESENT INVENTION

Figure 1:
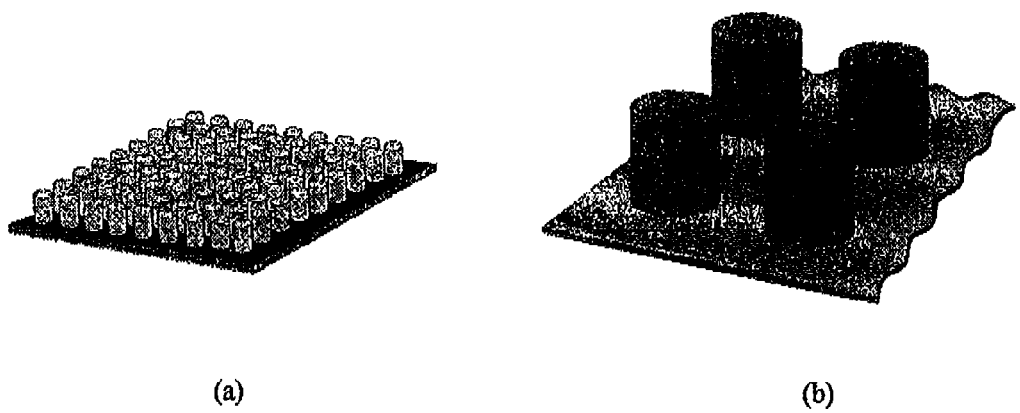
FIG. 1 shows a schematic diagram of gel posts of 1 mm diameter and 1.1 mm in height with (a) the 9×9 array of gel posts and (b) an enlarged diagram of four posts in the array.

The novel method and system described herein provides for the performance of PCR or other amplification or gene detection method in a gel medium less than 1 µL in volume, obtaining real-time data in situ by detecting the fluorescence of DNA in the presence of an intercalating dye or other means of product or amplicon detection. By performing replicate PCRs in multiple gel posts, statistical data to confirm a result can be obtained. The method of the present invention can be implemented for detection in the same sample of multiple nucleic acids, mutations/polymorphisms contained within a heterogeneous nucleic acid population, or multiple organisms, pathogens, bacteria or viruses within a single sample. The use of multiple different primers added to different gel posts allows a complete set of simultaneous tests, for example in clinical sample assays, with requisite positive and negative controls on the same gel post array to validate each test run. The multiple posts comprising a polyacrylamide, or other cross-linked polymer, hydrogel post array allow different posts to have different content, for example loading of differing oligonucleotide primers. Since nucleic acids are intended to be analyzed as a single specimen, the individual posts may contain different pairs of primers so they can amplify multiple sequences from the genome within a single post array without significant cross-contamination. Therefore the art is in need of a method and apparatus to perform multiple, essentially independent, nucleic acid amplification or detection reactions within a hydrogel post array, in which at least two different primer sets are present within the hydrogel post array.

As used herein, an "isolator" refers to a viscous component, as further described herein, mixed with at least one component intended to vary between posts within the hydrogel post array.

The system described herein is designed to facilitate performance of diagnostic tests in parallel on the same sample, using different posts in the same array. A non-limiting example of the utility of this platform is testing of patients as the patient presents in the clinic, for more rapid results, rather than transport of patient samples to a distant or centralized laboratory. This, advantageously, allows for samples to be tested individually, as needed, rather than being pooled or transported to distant laboratories for processing. The ability to acquire real-time PCR and MCA using the method and system of the present invention expands the use of this technique to applications such as isothermal amplification, allele-specific PCR or asymmetric PCR for mutation scanning and genotyping performed with unlabelled probes.

The novel in-gel PCR system of the present invention can perform PCR, melt curve analysis and real time quantitative PCR, with an output that compares favourably with conventional systems representing a "gold standard". Templates from a viral genome and from human genomic DNA are successfully amplified in the gel posts, with BK virus ("BKV"), by way of non-limiting example, readily detected in unprocessed sub-microliter volumes of urine from patients with BK viruria. Further, it is contemplated by the present invention that both processed and unprocessed clinical samples other than urine may be used with the present method and system, including but not limited to, serum, plasma, whole blood, sputum, mucous, aspirates, debrided tissue, scrapings and lymphatic fluid. Further, the present invention is not limited to use with only clinical samples from humans or animals, as the systems and methods described herein may use any sample which may contain a template for the amplification or detection as contemplated herein such as genetic or molecular characterization of bacteria, plant, mould, fungus or other lower-organism. The present invention contemplates use of methods for detecting a gene or transcript other than PCR and one skilled in the art would be aware of the variations of PCR and other gene or transcript detection systems.

The present invention provides a method of performing real-time PCR in gels with MCA in an array of cylindrical shaped self-standing gel posts (~0.64-0.86 µL per post). In a preferred embodiment the PCR and post-PCR analysis of the resulting amplified nucleic acid (if any) was performed in microfluidic volumes utilizing, in one embodiment, a 9×9 pattern of posts (FIG. 1). An inexpensive prototype heating device with a Peltier element was used for performing PCR and MCA, a diode laser for excitation of fluorescence, and detection optics containing a CCD, all of which controlled by a micro-controller. As well, the present invention provides the novel and desirable performance of in-gel amplification of templates from genomic DNA ("gDNA"), cDNA or RNA from human, animal, bacteria, plant, mould, fungus or other lower-organisms.

The gel of the present invention is contemplated to hydrophilic polymers forming colloidal hydrogel matrixes which result in similar mobilities of the nucleic acids of sizes contemplated by the present invention as in the specifically described gels herein, by way of non-limiting example, polyacrylamide cross-linked with bis-acrylamide and polyvinylpyrrolidone ("xPVP") cross-linked with PEG-diacrylate resulting from the photopolymerization of 3.3% vinylpyrrolidone with 0.7% Polyethyleneglycol-diacrylate.

The posts contemplated by the present invention may be cylindrical, spherical, conical or any other shape and dimension, so long as the posts of the array are physically separated, though they may be in fluid communication or in a common fluid substrate. The size and shape of the posts presented herein are presented as exemplar structures, and it is contemplated that a variety of moulds and therefore post shapes are possible. Also contemplated are inverted shapes placed on a planar surface, for example wells or depressions comprised of a hydrogel. Also contemplated are wells, depressions or capillaries made within a structure, for example plastic, glass, metal or other materials, filled with hydrogel.

There are significant disadvantages to the introduction of primers to individual posts within the post array through physical means. Primers present in a post forming part of a post array, as contemplated by the present invention, must be allowed sufficient time to diffuse throughout the hydrogel post prior to the nucleic acid sample to which the primers are intended to anneal, coming into contact with the post. As well, the primers within the post must be accurately introduced into the post so as to prevent cross contamination between the posts forming the post array; which is a challenge given the small volumes and limited spacing between posts as contemplated herein. Deposition of the primer mixture on a mold prior to introduction of polymer is of limited benefit, as the evaporation of the primer solution changes the localized salt concentration which thereafter affects the melting temperature of the PCR product and may even adversely impact the ability of the polymerase to catalyze PCR. It has been observed that in square arrays the primer solutions deposited within a planar mould results in evaporation on the outer edges at a rate faster than the innermost posts, and the rate of evaporation is difficult to control. Further, the prior art method of depositing primers in a well prior to the addition of polymerization reagents, disadvantageously resulted in rapid mixing with the gel when it is added and resulted in extensive cross contamination. Addition of primer components to the posts once polymerized is mechanically intensive and ensuring delivery of equal molarity of primers is technically challenging.

The present invention contemplates the deposition of primers to a mould, the deposition limited to a region consistent with, or internal to, a planned hydrogel post following a polymerization step as contemplated herein; wherein the primers are mixed with a viscous component for deposition, the viscous component selected from candidates including, but not limited to, carbohydrates, polymers or carbohydrate-polymer mixtures; such that following evaporation, the primer and viscous component forms a film on the mould which temporarily prevents primers from dissolving in the master mix during mould filling and covering; and allows polymerization of the hydrogel to occur while the primer and viscous components dissolves within the forming hydrogel post, and which will not interfere with the detection process used for the nucleic acids, as further described herein. As the primers are diffusing from within the polymerizing hydrogel post, the time needed for photo-polymerization is sufficient for the primers to distribute essentially evenly throughout the post. Following detachment of the mould and submersion of the array into oil or other medium, as contemplated herein, the posts have primers present within the individual posts. These primers are isolated from adjacent posts and do not cross-contaminate each other, enabling multiple amplification reactions using different nucleic acid primers or templates to occur on the same gel post array, including some posts that lack any primer at all (negative control). Although in one embodiment every post could harbour a different set of primers, in practice, other embodiments would be groups of posts that all have the same primer set (replicates) and/or primer sets arranged in a "checkerboard" pattern wherein each region of the checkerboard has a different set of primers to amplify a different template from the same sample. The viscous component and optional variable elements included therein, are referred to as the "isolator".

The present invention contemplates the use of various mono- and disaccharides as the viscous component, though in the preferred embodiment the viscous component is sucrose. Ones skilled in the art will recognize that a variety of agents, soluble in water and other than saccharides, are capable of being used as the viscous components, selected for their ability to temporally retard primers from dissolving into the unpolymerized hydrogel of the present invention on filling and covering, and further selected based upon their interaction with PCR and polymerization. Optionally, visible dyes may be added with the viscous component so as to allow visualization of evaporation and restriction of the associated primer to particular posts within the post array. In a preferred embodiment the viscous component has a pH greater than 7.0, so as to inhibit annealing of the primers during the evaporation; although other pH values are contemplated by the present invention, as well as the inclusion of components which inhibit annealing of the primers during evaporation.

EXAMPLE 1

Gel Polymerization

The polymerization of acrylamide gel for gel PCR can be initiated either by a photochemical method or by using peroxide. Adding ammonium persulfate (APS) as the initiator peroxide is the widely used method (Sambrook, J. & Russel, D. W.; *Molecular Cloning*, 3rd Edition ed.; CSHL Press, 2001). For photochemical polymerization, 'azobis' (2,2'-azobis(2-methyl-N-(2-hydroxyethyl) propionamide)) or riboflavin or Methylene Blue is added to the gel mix and the photochemical reaction is started by exposing the gel mix to ultraviolet light. It was noted that the polymerization initiator, APS, inactivated or inhibited the fluorescent intercalative dyes such as SYBR Green I and LC Green Plus that are needed for subsequent product detection by intercalative fluorescence, precluding addition of dye prior to the polymerization if the APS is used as the polymerization initiator. To circumvent this problem the gel posts were made by photopolymerizing the PCR reaction mix with LC Green Plus or SYBR Green, with or without template DNA, along with the acrylamide gel reagents in a glass mold having, for example, a 9×9 array of wells (FIG. 1). An alternate embodiment is to introduce the intercalating dye or other agent after completion of PCR or other amplification reaction. The wells were then sealed with a cover slip treated to promote gel adhesion. Once gel polymerization had occurred, the cover slip was detached from the mold along with the array of gel posts, and immersed in mineral oil to minimize evaporation, as described below.

EXAMPLE 2

Mould & Cover Slip Preparation

Figure 2:
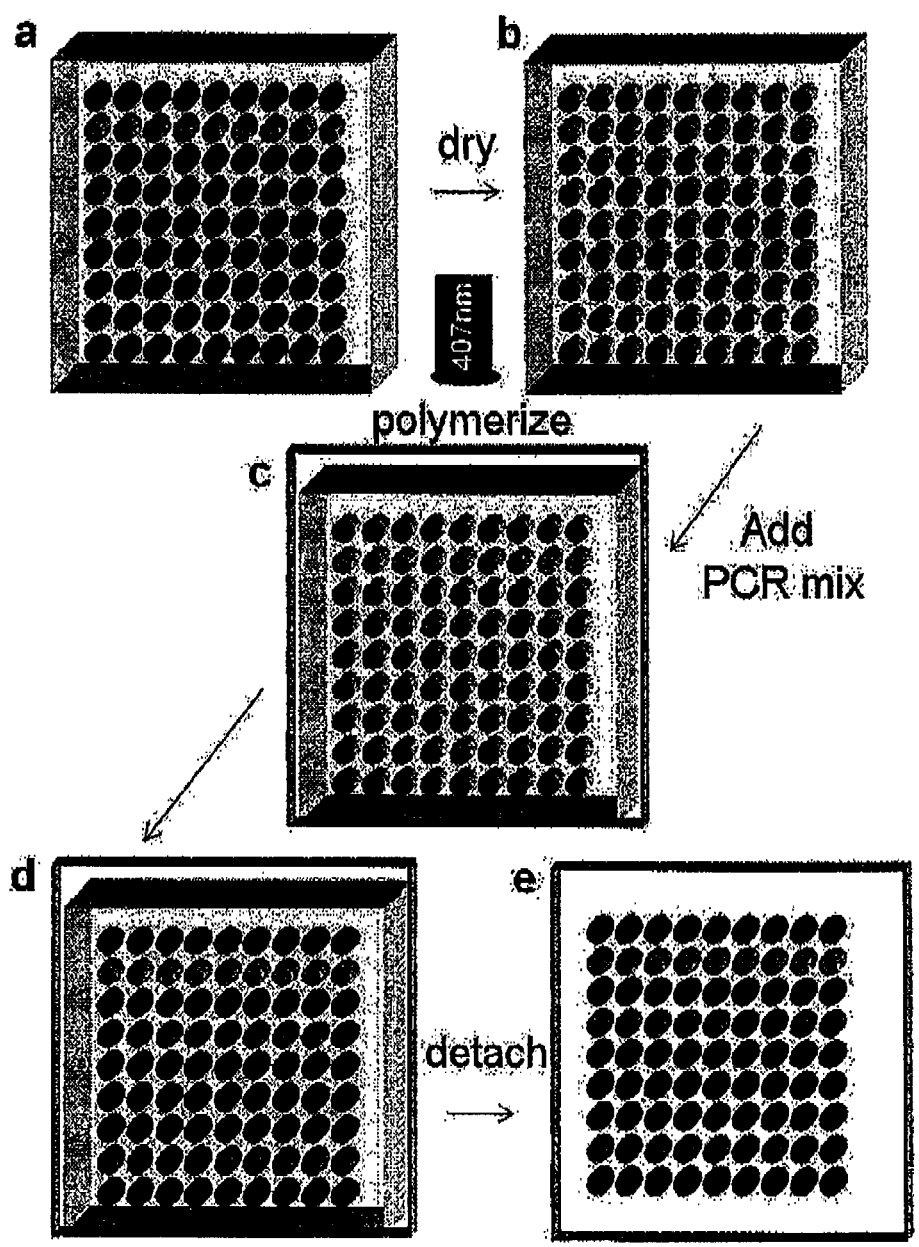
FIG. 2 shows multi-step preparation of multi-primed gel array.

FIG. 2 shows a summary of the steps associated with the preparation of the multi-primer hydrogel post array. Wells are filled with primer-isolator mix, FIG. 2(*a*); dried, FIG. 2(*b*); the PCR-polymerization mix is added and the mould covered with a cover slip, FIG. 2(*c*); after photo-polymerization, FIG. 2(*d*); the cover slip with hydrogel posts is detached from the mould, FIG. 2(*e*). The mould, approximately 20 mm×20 mm, is made with a 1.1 mm thick glass microscope slide permanently bonded to another 1.1 mm thick microscope slide with a 9×9 or 6×4 array of holes of cylindrical or conical shape 1 or 2 mm in diameter, although it is contemplated that other shapes of arrays and posts are also possible. Post arrays may be removed from the mould for use as reaction vessel, or in an alternate embodiment may remain within the mould or other support, for an enclosed reaction. Polyacrylamide gels of 2.8% to 12% are contemplated, with 2.8% being the softest gels reported for in-gel PCR.

To prepare the surface of the mould so that it would not adhere to the gels, a thin layer of Sigmacote (Sigma, St. Louis, Mo., cat#SL2) was spread onto the surface of the mould and left to dry. The mould was then washed with n-heptane (Applied Bio Systems, Foster City, Calif., cat #400079) and blown dry with air. In contrast, the surface of the cover slips (22 mm×22 mm, Fisher, Fair Lawn, N.J., cat#12-54B) were treated to enhance adherence to the gel by immersing them in a mixture of 40 mL of 95% ethanol, 1 mL of 100% acetic acid (Fluka, Buchs, cat# 45725), 8.9 mL of water, 100 μL of 3-(trimethoxysilyl)propyl methacrylate (Sigma, cat# 440159) for 1 hour followed by washing with isopropanol (2-propanol). After preparing the isolator, and casting a gel, the mould can be washed and reused for subsequent gel casting or the mould can remain permanently in contact with the gel. In another embodiment, the gel post array may be fully enclosed with a port for introduction of template and/or other reagents.

EXAMPLE 3

PCR/MCA Process, BKV PCR

In order to observe the characteristics of polymers and their effect on nucleic acid detection or amplification within hydrogel post arrays, hydrogel post arrays were prepared absent the use of the isolator contemplated by the present invention. After depositing primers in the isolator, the gel can be polymerized with or without template DNA included in the polymerization mixture. In the latter case, the DNA can be added atop the gel posts where it diffuses into the gel before PCR is performed. One hundred μL PCR gel mix contained 47 μL PCR reagents, 10 μL gel reagents and 43 μL water. The 47 μL PCR reagents were: 20 μL of 5×PCR buffer (333 mM tris-sulphate, pH 8.6, 83 mM $(NH_4)_2SO_4$ (Sigma); and 40% sucrose (Sigma)), 4 μL of 50 mM $MgCl_2$ (Fluka), 2 μL of -10mM [dNTPs] (Sigma), 2 μL of 1% bovine serum albumin (Sigma), 2 μL of 10 μM primer solution (Integrated DNA technologies, San Diego, Calif.) for each of 2 primers to produce 100 base pair ("bp") product, 2 μL BKV template DNA either before or after polymerization, 10 μL of 10×LC Green Plus (Idaho Technology Inc., Salt Lake City, Utah) and 3 μL of Taq polymerase (20 units/μL). The 10 μL of gel reagents were: 7 μL of a 40% acrylamide (Sigma, cat #A9099)+4% bis-acrylamide aqueous solution (N,N-methylene bisacrylamide, BioRad, Hercules, Calif., cat# BA05-1610201), 2 μL of 3% azobis (Wako, Richmond, cat#VA-086), and 1 μL of 10% TEMED (N,N,N',N'-tetramethylethylenediamine, Sigma, cat#T7024). This mixture was degassed in vacuum and pipetted into the wells in the mold. Once all the wells were full, a 22 mm×22 mm cover slip treated, as noted above, for adherence to the acrylamide was slipped atop the wells. The isolator prevents cross contamination of different primer sets during this step. The mold with the cover slip atop was then exposed to the 405 nm laser (~4 $mW/cm^2$ on the posts) for 25 min in order to photopolymerize the acrylamide mix. The cover slip with the attached posts was then slowly lifted from the mould, immediately immersed in mineral oil (Sigma, cat# M5904) in a shallow anodized aluminum 23 mm×23 mm pan (posts facing up), and placed on the Peltier element. Thermal cycling was performed with an initial denaturation of 30 s at 94° C. followed by 50 cycles of denaturation at 94° C. for 15 s, annealing at 52° C. for 30 s, and extension at 72° C. for 30 s, and ending with an extension step of 72° C. for 60 s. After completion of PCR, MCA was performed. To determine the threshold for BKV amplification, BKV PCRs were performed with 34 to 8640 BKV copies/post. Overall, a total of 52/52 independent experiments to amplify BKV were successfully performed on gel posts, confirming reproducibility of the method.

In order to show that PCR can be performed with unprocessed samples, PCR was performed with 1.5 μL of raw urine added to the PCR reaction mix prior to the polymerization. All the PCR parameters are similar to the BKV DNA PCR other than the PCR cycle number was reduced to 35.

For addition of template after polymerization of gel posts, a similar PCR gel mix (as above) was made without BKV DNA and polymerized. After the gel was detached from the mould, a 14 μL BKV template (2.86 ×$10^7$ copies/mL) was added atop the gel posts and the DNA allowed to diffuse for 30 min in a covered Petri-dish before performing PCR with the same thermal cycle conditions as above. If the DNA added atop the gel was uniformly absorbed, the amount of template DNA was 4,900 BKV copies/post. Real time quantitative PCR confirmed that the same template copy number was detected for template polymerized within the gel or added atop the gel. In order to study the size limitation of the product that could be amplified in a given gel concentration, we have also performed BKV PCR (17,280 BKV copies per post) with a series of different primers (Table 1), with the template DNA polymerized in the gels as indicated above.

TABLE 1

Primer sequences for BKV and HPA1 amplification by PCR

| Primer description | SEQ ID | Product length (bp) | Sequence |
| --- | --- | --- | --- |
| BKV reverse | SEQ ID NO 1 | | 5'-aaacaccctaacctcttctac-3' |
| BKV forward | SEQ ID NO 2 | 100 | 5'-ttccttttgctaagtgacc-3' |
| | SEQ ID NO 3 | 150 | 5'-tattttaagatccgcctga-3' |
| | SEQ ID NO 4 | 200 | 5'-gcctgtttactaacagctctg-3' |
| | SEQ ID NO 5 | 250 | 5'-gcctctttgtaaagctgatag-3' |
| | SEQ ID NO 6 | 300 | 5'-catgtgaccaacacagctac-3' |
| | SEQ ID NO 7 | 350 | 5'-ctaggtattttgggactttca-3' |
| | SEQ ID NO 8 | 400 | 5'-tgcttatccagttgagtgc-3' |
| | SEQ ID NO 9 | 450 | 5'-ccagtcccaggtaatgaatac-3' |
| | SEQ ID NO 10 | 500 | 5'-gaattacaggtcaaagtaccc-3' |
| | SEQ ID NO 11 | 600 | 5'-gtgcatgagcatggtgga-3' |
| | SEQ ID NO 12 | 800 | 5'-aagctaagtgctgaaaatgac-3' |
| | SEQ ID NO 13 | 1000 | 5'-cccaaccaaaagaaaagg-3' |
| HPA1 reverse | SEQ ID NO 14 | | 5'-cacagcgaggtgagcc-3' |
| HPA1 forward | SEQ ID NO 15 | 42 | 5'-ctcctgtcttacaggccc-3' |
| FGFR reverse | SEQ ID NO 16 | | 5'-gctgacttctatttatataacttcaagc-3' |
| FGFR forward | SEQ ID NO 17 | | 5'-cagaagtttttgagagtggcatgatg-3' |
| HSV1 reverse | SEQ ID NO 18 | | 5'-cgccggcggatacgaagacg-3' |
| HSV1 forward | SEQ ID NO 19 | 174 | 5'-cgtcgcgggttggccacata-3' | transport medium (Copan Diagnostics Inc. Murrieta Calif.) diluted with 21 µl of 1×PCR buffer was applied on the top three rows of the hydrogel well array (one half of the total number of hydrogel filled wells) for 10 min. A multiplicity of sample treatment protocols for application to gel posts can be envisaged by one skilled in the art who would recognize that

EXAMPLE 4

PCR/MCA from a Clinical Sample in Gel-fFilled Wells

A glass mould 6×4 was prepared as described in example 2, filled with 0.2 µM HSV1 primers (Table 1) in 8% Trehalose and dried for 1 hr. Then PCR gel mix was added into the wells.

Figure 6:
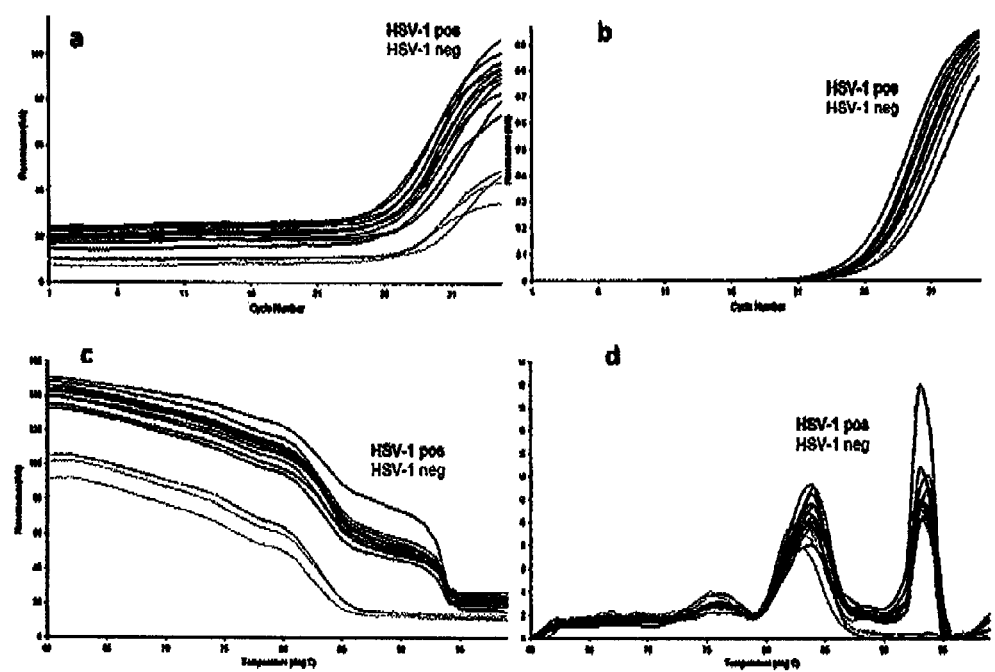
FIG. 6 shows PCR and MCA results for Herpes Simplex virus 1 in a genital swab made with primers sequestered in gel-filled wells with (a) raw and (b) normalized PCR, and MCA charts with positives coloured blue and negative green based upon (c) fluorescence and (d) derivative excitation.

One hundred 4 PCR gel mix contained 41 µL PCR reagents, 13 µL gel reagents and 43 µL water. The 47 µL PCR reagents were: 20 µL of 5×PCR buffer (333 mM tris-sulphate, pH 8.6, 83 mM $(NH_4)_2SO_4$ and 40% sucrose, 4 µL of 50 mM $MgCl_2$, 2 µL of 1% BSA, 10 µL of 10×LC Green Plus and 3 µL of Taq polymerase (20 units/µL). The 10 µL of gel reagents were: 10 µL of a 40% acrylamide+4% bis-acrylamide aqueous, 2 µL of 3% azobis and 1 µL of 10% TEMED. The reagent suppliers are same as in example 3. A cover slip was then slid over the mould and acrylamide was photo-polymerized for 22 min under 360 nm UV lamp (UVG L25, UVP, Upland, Calif.). The cover slip was then removed and 4 µL of a clinical sample arising from immersion of a genital swab in Universal the final volume depends on the number of gel posts to which the sample is applied. The sample was removed and the mould was then immersed in mineral oil in aluminum pan. Thermal cycling was performed with an initial denaturation of 90 s at 96° C. followed by 35 cycles of denaturation at 94° C. for 30 s, annealing at 63° C. for 40 s, and extension at 72° C. for 35 s, and ending with an extension step of 72° C. for 120 s. After completion of PCR (FIG. 6 (a) and FIG. 6(b)), MCA was performed (FIG. 6 (c) and FIG. 6(d)). Negative samples demonstrate separation from positive within FIG. 6 as the lower, light-gray, lines within the individual graphs and positive samples represented by the darker lines above.

EXAMPLE 5

PCR/MCA Process, Genomic DNA PCR

Extending the principles from Example 3, similar PCRs were performed with purified gDNA added to the gel before or after the polymerization. Overall, gDNA has been successfully amplified in gel posts for 27/27 independent experiments. For the PCR performed with gDNA template polymerized in the gel, a 42 bp product from human HPA1 (human platelet antigen 1) was amplified. Except for the template and oligonucleotide primers (as listed in Table 1), the PCR reaction mix was similar to that for the BKV PCR. 225 ng of gDNA was added to the 100 μL mix (~2.2 ng per post). PCR thermal cycling conditions were as indicated for the BKV PCR.

For the PCR performed with gDNA added atop the polymerized gel, a 71 bp product from the FGFR2 gene from human gDNA was amplified. Primers used for FGRF2 amplification were forward primer SEQ ID No. 16 (5' "CAGAAGTTTTTGAGAGTGGCATGATG") and reverse primer SEQ ID NO 17 (5' "GCTGACTTCTATT-TATATAACTTCAAGC"). Fourteen μL of gDNA (30 ng/μL) was pipetted onto the whole array of posts and was left in a covered Petri-dish for 30 min to allow diffusion of gDNA into the gel. If all the gDNA was uniformly absorbed, a DNA amount of ~5 ng/post is predicted.

EXAMPLE 6

PCR/MCA Instrumentation

Figure 3:
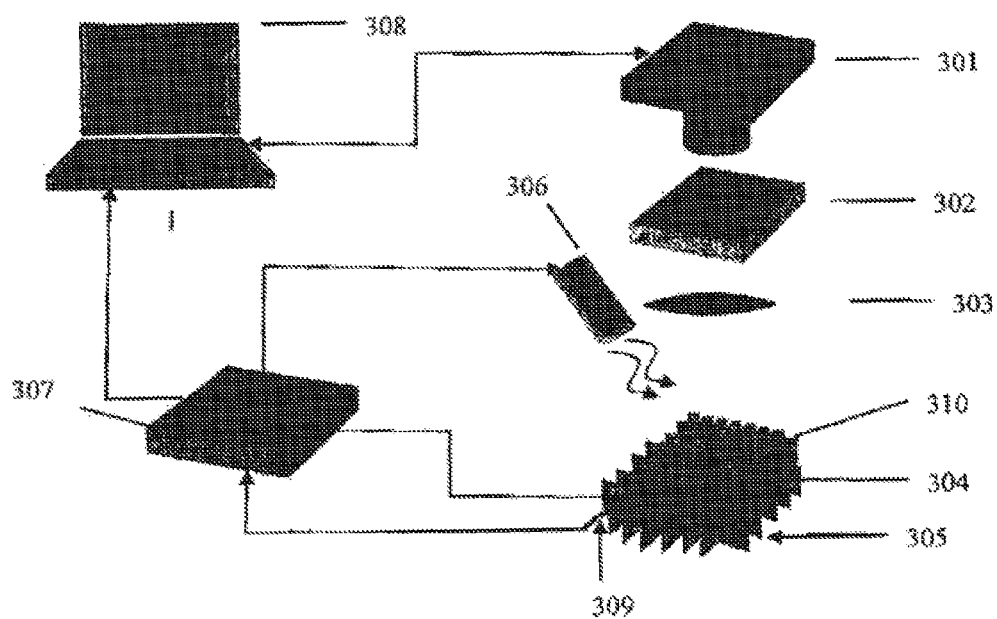
FIG. 3 shows a schematic diagram of the instrument used for performing PCR and MCA.

An inexpensive prototype instrument (shown in FIG. 3) is used to perform the PCR reaction in the gel posts. This instrument uses Motorola 68332 microprocessor 307 to control Peltier element 304 (XLT2398-01L, Marlow Industries, Dallas, Tex.) to perform heating and cooling for PCR and MCA, where Peltier element 304 is placed in thermal communication with hygrogel array 310 and heatsink 305. A charge-coupled device ("CCD") camera 301 (Deep Sky Imager, Meade, Irvine, Calif.) is mounted above Peltier element 304 as well as hydrogel array 310. 65 mW 405 nm laser diode 306 (DL-7146-101S, Sanyo) is mounted at a 70 degree angle to horizontal for a fluorescence excitation source. Laser diode 306 delivers an average of 32 μW of excitation power to each post within hydrogel array 310. 50 nm wide band-pass interference filter centered at 510 nm 302 (BP510/50, Chroma Technology, Bellows Falls, Vt.) is mounted in front of the camera to attenuate excitation light. Biconvex lens 303 (KBX046, Newport, effective focal length 25.4 mm) is mounted between filter 302 and hydrogel array 310. Camera parameters such as the exposure time, light and dark levels are set by the user on PC computer 308, in electronic communication with microprocessor 307. During PCR, once the extension temperature is reached, laser diode 306 is switched on and a fluorescent image of the gel posts is taken by CCD camera 301 and stored by computer 308. During the MCA, laser diode 306 is left on continuously and an image is taken by CCD camera 301 and stored by computer 308 at each degree from 50° C. to 95° C., once the chip has been stabilized at a particular temperature. The system is calibrated by placing calibrated thermocouple 309 (5TC-TT-K-40-36, Omega Engineering Inc., Stamford, Conn.) between the hydrogel posts within hydrogel array 310, under the oil. The settings on the system are then correlated to the observed temperatures of the calibrated thermocouple. Microprocessor 307 is in electronic communication with, and controls, Peltier element 304, temperature sensor 309 and laser diode 306.

EXAMPLE 7

PCR and Melting Curve Analysis

The CCD images acquired at the extension step of each PCR cycle (total of 50 images) were analysed with ImageJ software (National Institutes of Health, USA) using the MicroArray Plug-in (Dr. Robert Dougherty, OptiNav Inc., Redmond, Wash.) that can be used to plot the cycle number vs. the fluorescence intensity of each post. Even though the mould disclosed herein creates a 9×9 array of posts, optical limitations of the CCD assembly allow image acquisition for only a 6×8 array. In order to determine the efficiency of the PCR, most commercial real-time quantitative PCR instruments embed some proprietary version of data processing in their software. All reported methods characterize the real-time PCR curves by applying curve fitting and determining the threshold values where the fluorescence of the PCR begins to rise above the background signal and the DNA copy numbers can be seen to increase exponentially.

Therefore a sigmoid was fitted to the real-time PCR curves in order to find the exponential region and to find the threshold value, termed the "crossing point" (CP). A Linear Regression of Efficiency or LRE method (Rutledge, R. G. & Stewart, D. BMC *Molecular Biology* 2008, 9) modified with a linear baseline correction (Rebrikov, D. V. & Trofimov, D. Y. *Applied Biochemistry and Microbiology* 2006, 42, 455-463) to fit the sigmoid.

With LRE, the fluorescence of the DNA, $F_c$ at cycle c of the PCR can be written as $$F_c = \frac{F_{Max}}{1 + \left(\frac{F_{Max}}{F_0} - 1\right)(E_{Max} + 1)^{-c}} + F_B + cF_K \qquad \text{Formula 1}$$

where $F_o$, $F_{Max}$, $F_B$ and $F_K$ are the fluorescence values for the initial reaction, endpoint reaction, constant background and variable background, and $E_{Max}$ is the maximum amplification efficiency. A linear baseline to the equation was used to facilitate baseline subtraction with the last two terms of the equation, $F_B$ and $cF_K$. The maximum of the second derivative of the sigmoid is determined to calculate the $C_P$ value, representing the cycle number at which the fluorescence has risen above the background level and the exponential growth of the PCR is at a maximum.

The algorithm of Formula 1, was implemented into computer code using visual basic for applications 6.3 in Microsoft Excel, which receives the fluorescence intensities obtained from the text file output by the ImageJ software and returns multiple plots including the raw, fitted, and normalized data. $C_P$ values for each PCR reaction are also calculated for each post. FIG. 4(a) shows real-time data (experimental data points connected by interpolated lines) for 36 posts that were obtained after PCR performed with 3,456 starting copies of BKV DNA template per post in a 2.8% polyacrylamide gel. Insets in FIG. 4(a) show CCD images of the gel array at the $1^{st}$ cycle, $30^{th}$ cycle, and $50^{th}$ cycle. These results were confirmed in more than 10 independent experiments and no fluorescence above background was detected in the negative controls FIG. 4(b) and FIG. 4(c) show the plots produced by the algorithm and the $C_P$ values for each post respectively.

There is spatial variation in the illumination of the post array due to the oblique incident angle and intentional optical diffusion of the laser. As a result, fluorescence excitation is not uniform on all posts, and thus each real-time PCR curve starts at a different intensity level as seen in FIG. 4(a). These background variations are removed by data processing to produce the normalised curves of FIG. 4(b). Considerable background light between posts is observed, as shown in the inset post array image for the 50th cycle in FIG. 4(a). This background is due to a thin film of gel that remains between the posts as the gel post array is assembled, and where PCR also occurs. One skilled in the art would recognize that modification of assembly protocols would remove or reduce this thin film, and it is contemplated that the present invention also encompasses such modified assembly protocols. Despite the presence of the thin gel layer, fluorescence data is largely independent of the background as they result from the summation of pixels entirely within each post. As disclosed herein, the present invention does not suffer from "cross-talk" between posts.

Melting of the DNA was performed immediately after the PCR was completed. The melting curves were obtained by measuring the fluorescence in the CCD images obtained at each degree from 50° C. to 95° C. as seen in FIG. 5(a). The negative derivative of the fluorescence with respect to the temperature was plotted in FIG. 5(b) and allowed the melting temperature of the PCR products ($T_m$) to be determined as the temperature at the peak 31. The melting temperature for BKV amplicons (average $T_m \pm 1$ σ for all 36 traces) was 82.6±0.4° C. The sequence of BKV PCR product was confirmed by sequencing the DNA from one post. Part of the sequence is shown in FIG. 5(c) with sequencing performed with ABI 3130×1 DNA capillary analysis system (Applied Biosystems, Foster City, Calif.). As for the real-time PCR traces in FIG. 4(a), the melting curve baselines of FIG. 5(a) are influenced by the heterogeneous laser illumination; this bias is removed through the data differentiation used to produce FIG. 5(b). Also in keeping with FIG. 4(a), the inset image for 75° C. shows considerable background fluorescence, owing to the thin layer of gel that remains between posts. Insets in (a) show the CCD images of the gel array at 75° C. and 85° C. These results were confirmed in more than 10 independent experiments.

Figure 4:
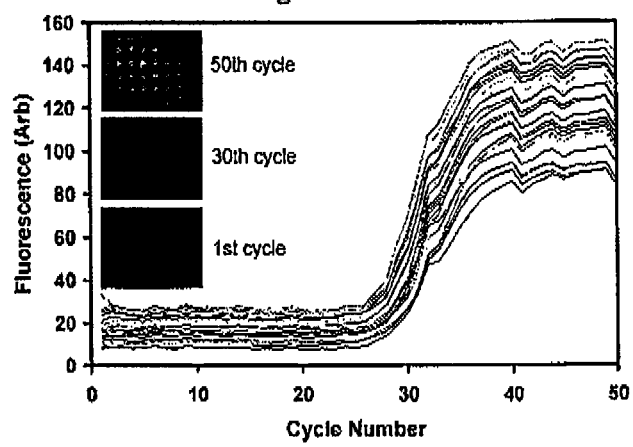
FIG. 4 shows real-time PCR in gel posts arrays with (a) raw fluorescence data obtained by CCD image, (b) processed data as contemplated herein and (c) $C_P$ values obtained for each post.
Figure 4:
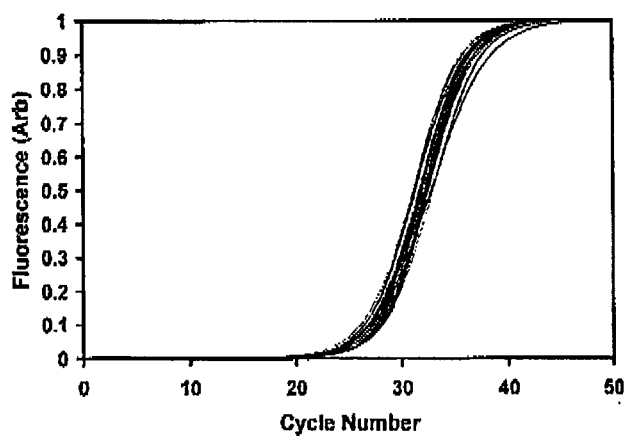
Figure 4:
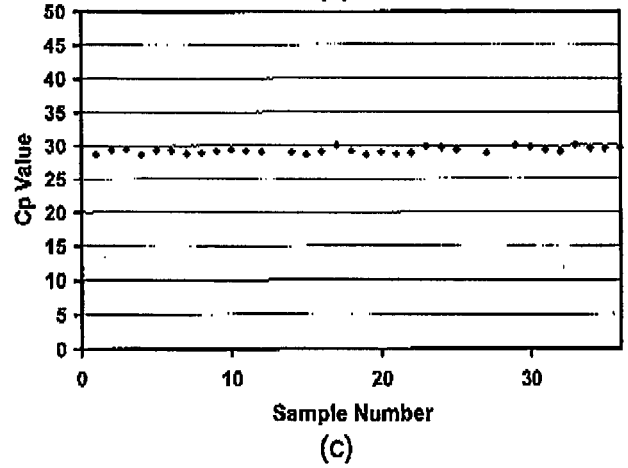
Figure 5:
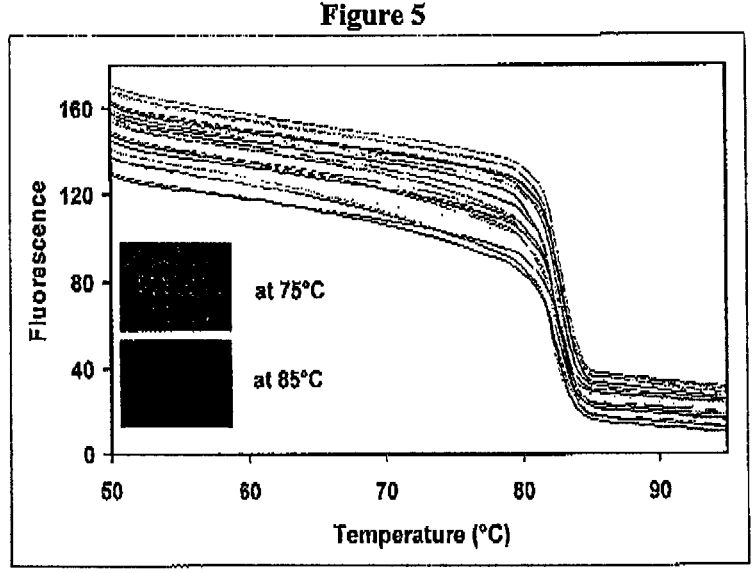
FIG. 5 shows product detection in gel post arrays using melting point analysis with (a) melting curves of BK virus (BKV) amplicons in gel posts represented in FIG. 4, (b) the negative derivative of fluorescence versus temperature showing the melting point of the PCR product and (c) part of the sequence of the product.
Figure 5:
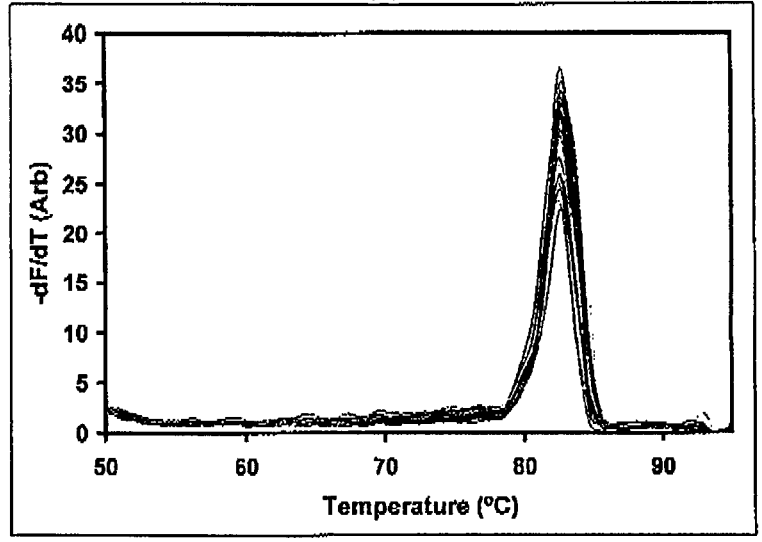
Figure 5:
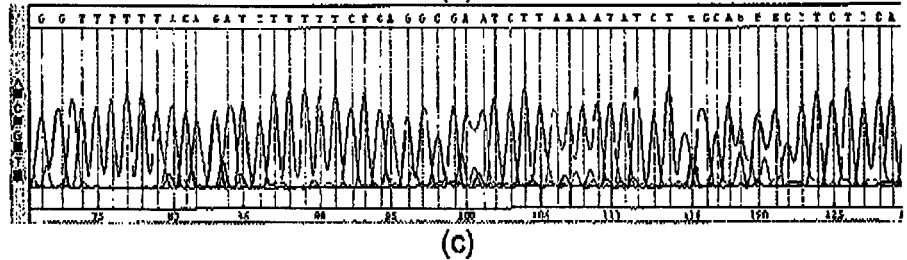

The results shown in the FIG. 4 and FIG. 5 were acquired with the gels polymerized with the BKV DNA template inside. However, if this technology is to be applied to real-world medical diagnostics, adding clinical samples to the pre-cast gel is likely to be a better approach. PCR with a BKV DNA template that was allowed to diffuse into a pre-cast gel matrix was performed and real-time PCR curves obtained, as shown in FIG. 7(a). This confirms that exogenous template DNA can successfully enter the gel and interact with the embedded PCR components. The melting curve analysis data is shown in FIG. 7(b); for the experiment shown, the average melting temperature was 82.8±0.6° C.

EXAMPLE 8

Effect of the Gel Concentration on the PCR Product Size

In order to study the limitations of PCR product lengths in polyacrylamide gels, a series of BKV products with lengths from 100 to 1000 bp in 5 different gel concentrations were amplified absent isolator, using the method described in Example 3, with template DNA added prior to polymerization and primers added before polymerization using the isolator method described herein. Table 2 shows PCR amplification of different lengths of BKV template in different polyacrylamide gel concentrations, with a (+) sign indicating that PCR product was detected. Thirteen different primer sets were used to amplify different sized segments of a BKV template, using 5-6 different primer sets per gel post array (see Table 1). Primers were added to the moulds prior to polymerization (isolator method). Results were confirmed with at least two experiments for each primer set and the sizes of the PCR products were confirmed by running vertical in situ gel electrophoresis on each post. Each array included several different primer sets, deposited by the isolator method, for distinct sets of gel posts, demonstrating simultaneous multiparameter testing. The results demonstrate that the gel limits the size of the product that can be amplified. As the gel concentration increases, the maximum product size that can be amplified decreases suggesting that the smaller pore size of harder, high concentration gels restricts movement of the larger reagent molecules (DNA template, polymerase etc.) inside the gel as compared to their movement in lower concentration, softer gels. The size limits shown in that table are appropriate for PCR annealing and extension times of 30 s as postulated in Example 3.

TABLE 2

BKV template amplification length, gel concentration and cross-talk controls.

| Size of Amplicon (bp) | Concentration of Polyacrylamide | | | | |
|---|---|---|---|---|---|
| | 4% | 6% | 8% | 10% | 12% |
| 100 | + | + | + | + | + |
| 150 | + | + | + | + | + |
| 200 | + | + | + | + | + |
| 250 | + | + | + | + | + |
| 300 | + | + | + | + | + |
| 350 | + | + | + | + | + |
| 400 | + | + | + | + | + |
| 450 | + | + | + | − | − |
| 500 | + | + | − | − | − |
| 550 | + | − | − | − | − |
| 600 | + | − | − | − | − |
| 800 | − | − | − | − | − |
| 1000 | − | − | − | − | − |

In order to show that the primers do not diffuse from one post to another, a separate experiment was performed in which a single primer set was added to some but not all wells prior to the addition of the gel polymerization mix as described in Example 4 to create a checkerboard of adjacent positive and negative controls. Table 3 shows positive posts have PCR amplification of 100 bp PCR fragment in 6% polyacrylamide gel while negative posts lacked the primer to allow amplification. The lack of amplification observed confirms that cross-talk is suppressed. No product was obtained for posts lacking primers, indicating that when using the isolator method described herein, cross-contamination by primers does not occur. Diffusion of PCR components between posts was not detected.

TABLE 3

Cross-talk controls via checkerboard of alternating positive and negative posts.

| posts with primers (100 bp) | posts without primers |
|---|---|
| + | − |

EXAMPLE 9

Quantitative PCR

Figure 7:
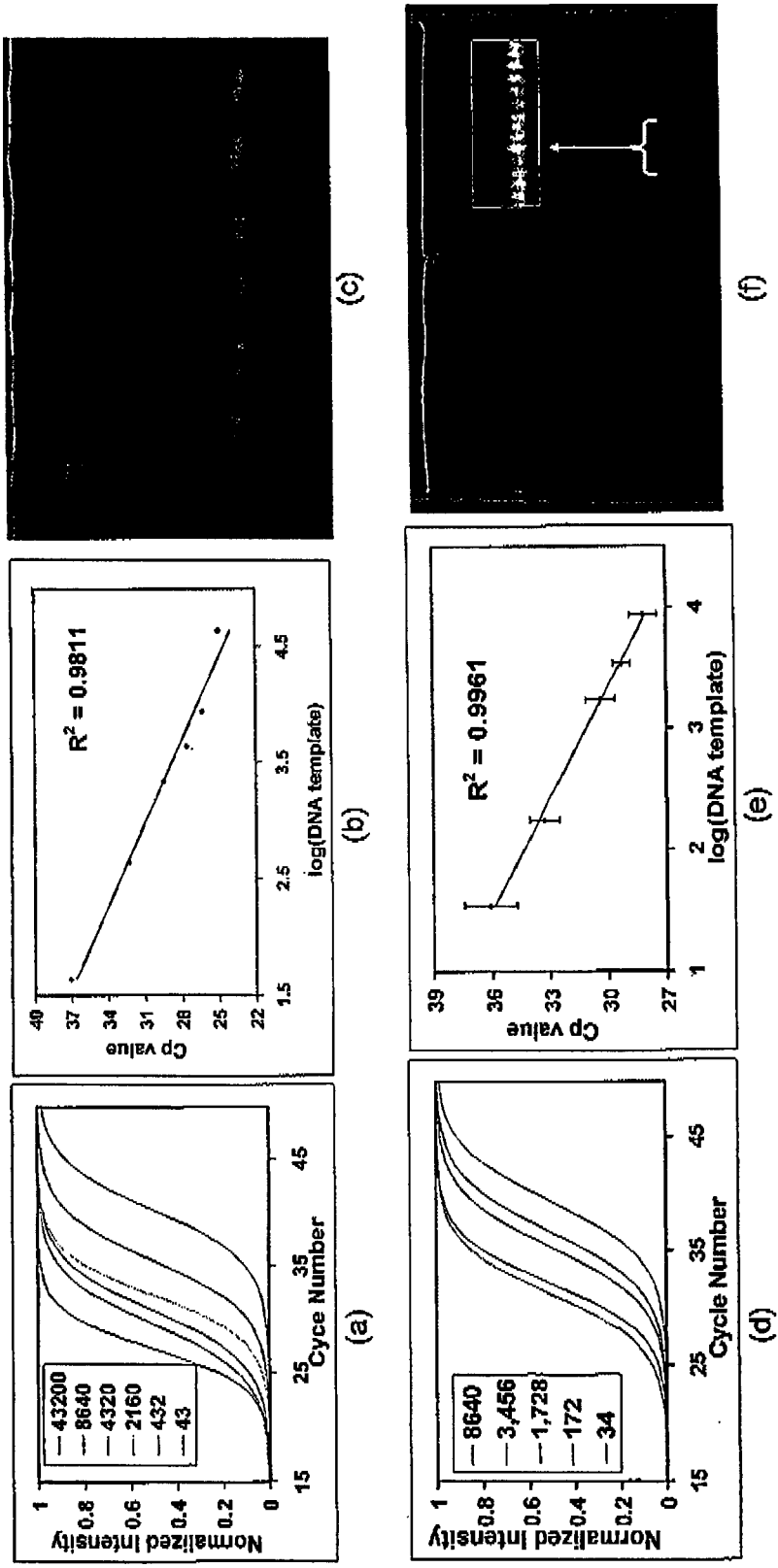
FIG. 7 shows a comparison of BKV DNA PCR in a 2.8% polyacrylamide gels performed in a Lightcycler® (a-c) or gel posts (d-f) in particular (a) Lightcylcer® real-time PCR intensity (b) Lightcylcer® $C_P$ values versus logarithm of DNA quantity per 0.85 mL reaction, (c) size confirmation of the Lightcylcer® amplified products in a vertical polyacrylamide gel, (d) gel post real-time PCR intensity (e) gel post $C_P$ values versus logarithm of DNA quantity per 0.85 µL, reaction, (f) size confirmation of the gel post amplified products in a vertical polyacrylamide gel.

In order to characterize quantitative real-time PCR in gel posts, different amounts of BKV DNA were tested under the same PCR conditions to amplify a product of 100 bp in 2.8% polyacrylamide gel posts. For comparison, conventional real-time PCR with the same template was carried out in the Lightcycler®, an instrument that is routinely used for melt curve analysis in clinical diagnostic laboratories and provides a clinically relevant "gold standard". For the Lightcycler® PCR, PCR reaction/gel mixes were polymerized in capillaries in order to mimic the PCR in the gel posts and held a total volume of 0.64 - 0.84 µL per reaction, similar to gel posts, though smaller volumes are also contemplated. FIG. 7(a-c) shows real-time PCR data generated by the Lightcycler®, relationship of $C_P$ values versus log $[DNA]_{initial}$ and the confirmation of the product size by vertical gel electrophoresis. The analogous results of FIG. 7(d-f) obtained with the in-gel post PCRs mirror those of FIG. 7(a-c) from the Lightcycler®. Each post was picked up individually and placed above the gel before running electrophoresis as shown in FIG. 7(f), with a 100 bp DNA ladder shown in the middle in FIG. 7(f) and on the left in FIG. 7(c). The results below confirm that melt curve analysis of PCR in gel posts matches that from gold standard testing.

FIG. 7(b) and FIG. 7(e) show that, as expected, the $C_P$ values decrease linearly with the logarithm of increasing template DNA copy number for the Lightcycler® and gel post array, respectively, and that the relationship is comparable in the two systems (within ~1 cycle). The melting temperature of the products in the Lightcycler® is 81.5° C. which agrees with the gel posts value of 82.6° C. Both real-time PCR and MCA validate the PCR conditions in gel posts. The inset in FIG. 7(f) is an enlarged section of the gel band, showing individual bands from each gel post. The samples loaded to electrophoresis lanes shown in FIG. 7(f) were from PCR performed with an initial 3456 BKV DNA templates per post.

EXAMPLE 10

Genomic DNA PCR

Figure 8:
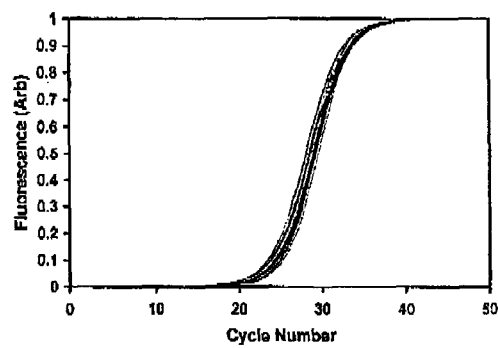
FIG. 8 shows amplification of a target sequence from human genomic DNA by PCR in 2.8% polyacrylamide gel posts with (a) real-time PCR curves for HPA1, (b) melting curve analysis for HPA1, (c) real-time PCR curves for FGFR2 and (d) melting curve analysis for FGFR2.
Figure 8:
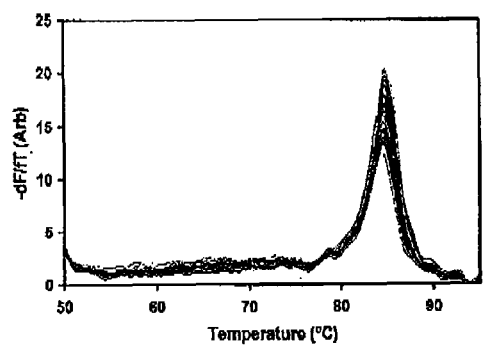
Figure 8:
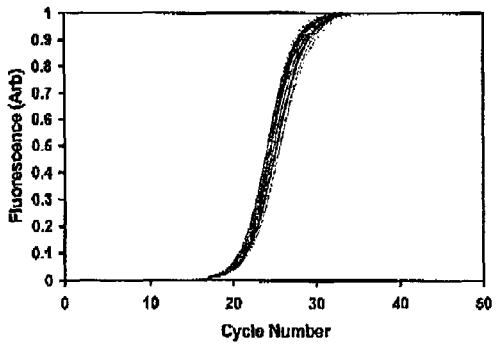
Figure 8:
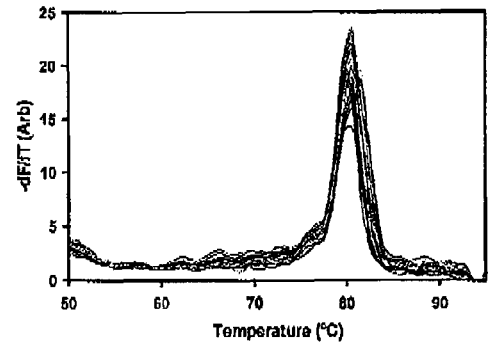

Human gDNA is made of 3 billion base pairs of DNA, as compared to viral DNA, or plasmid DNAs that are only a few thousand to hundreds of thousands of base pairs in size. During PCR, there is a great deal of heterogeneous non-target DNA present in the long gDNA compared to the uniformity of short plasmid DNA, suggesting that the efficiency of the gDNA PCR is less than that of plasmid DNA. The prior art with respect to gel PCRs used plasmid DNA or cDNA as the template but not gDNA. Two gDNA PCR were undertaken in 2.8% polyacrylamide gel, one with the gDNA polymerized in the gel and one with the gDNA added after polymerization of the gel.

gDNA was subjected to PCR to amplify a 42 bp product containing a known SNP from the human HPA1 gene in the gDNA template polymerized inside the gel, using SEQ ID NOs 14 and 15 as primers; as otherwise shown in Table 1. The template was chosen in anticipation of future genotyping with the gel posts using e.g. allele specific PCR as previously shown. The processed real-time PCR curves and the melting curve analysis data are shown in FIG. 8(a) and FIG. 8(b) respectively. The amount of genomic DNA in the HPA1 PCR is ~2.2 ng per post. PCR was then performed with gDNA template (~5 ng/post) added after the gel polymerization, the gDNA allowed to diffuse into the gel matrix. For the latter approach, the FGFR2 gene from human genomic DNA, with amplification of a 71 bp product also containing a known SNP using SEQ ID NOs 16 and 17 as primers. FIG. 8(c) shows the processed real-time PCR curves while FIG. 8(d) shows the melting curve data for the FGFR2 PCR. Both HPA1 and FGFR2 product sizes were confirmed by vertical gel electrophoresis. This is the first use of gDNA for gel PCR, where gDNA is introduced to the gel mix either prior to or after the polymerization.

EXAMPLE 11

Primers Incorporated into a Post Array in Checkerboard Pattern

A hydrogel post array was prepared in checkerboard pattern using an isolator comprised of 8% sucrose, 1% Dextran T500, 13 mM Tris-base, 0.05% NP-40, 0.05% Tween20 and 0.2 µM of each primer and BKV DNA (~3,000 molecules per post) or no DNA. The isolator mixture has a pH of 10.6, which advantageously inhibits primer annealing during the evaporation of the isolator, FIG. 2(a) and FIG. 2(b). Mould heights of 1.1 mm were used and following polymerization, FIG. 2(c) and FIG. 2(d), detachment from the mould, FIG. 2(e), and immersion into oil; PCR (FIG. 8(a) and FIG. 8(b)) was undertaken with monitoring of the PCR through melting curve analysis (FIG. 8(c)). A vertical 8% polyacrylamide gel electrophoresis (FIG. 8(d)) demonstrated specific PCR product in positive posts and variations of primer dimer in no-template posts.

EXAMPLE 12

Alternate Polymers for Isolator Mixture

Figure 9:
FIG. 9 shows an (a) amplified PCR product from BKV template applied in checkerboard pattern with isolator; (b) qPCR and (c) MCA analysis of positive and negative posts demonstrating a clear separation of curves and (d) an 8% polyacrylamide gel electrophoresis of DNA in posts showing the specific (111 base pair) and non-specific PCR products.
Figure 9:
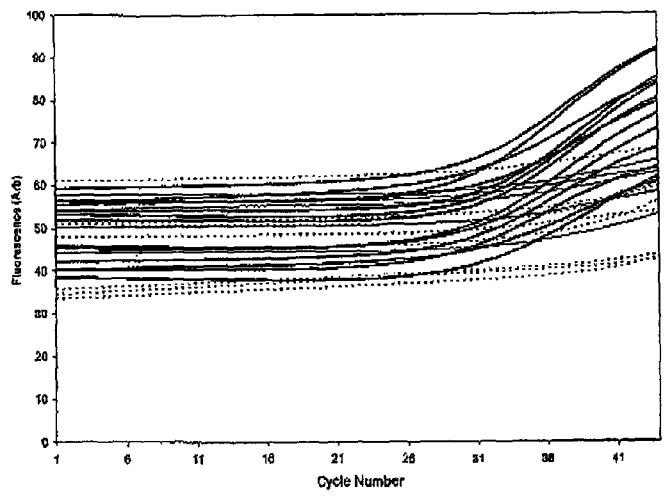
Figure 9:
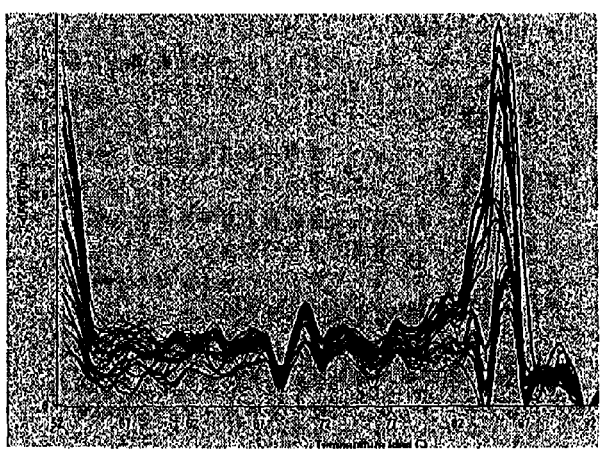
Figure 9:
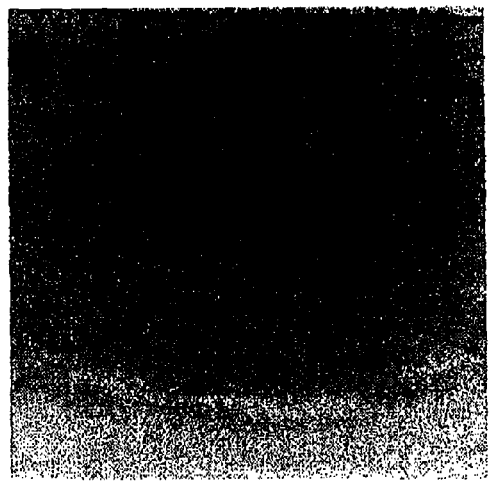
Figure 10:
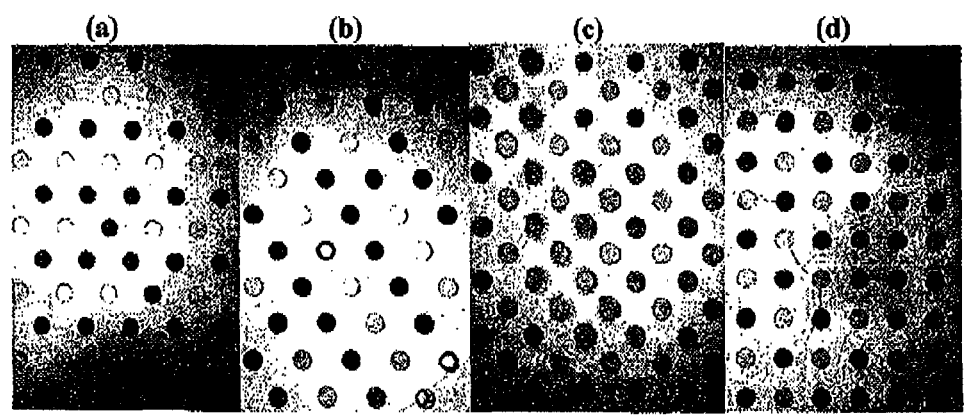
FIG. 10 shows the effect of polymer component of isolator on cross-contamination between hydrogel posts using (a) 1% linear polyacrylamide (b) 1% Dextrane 500 (c) 1% Ficoll 400 and (d) 1% polyethyleneglycol Carbowax 8000.

Alternate polymers were compared in a preparation of 1% polymer with 8% sucrose, with thinner molds designed to result in hydrogel posts of 0.5 mm as opposed to the 1.1 mm used in other experiments disclosed herein. FIG. 9 shows a comparison of four hydrophilic PCR-compatible polymers, linear polyacrylamide (FIG. 9(a)), Dextran T500 (FIG. 9(b)), Ficoll 400 (FIG. 9(c)) and polyethylene glycol Carbowax 8000 (FIG. 9(d)); and visually demonstrates their ability to temporally prevent dissolving of the evaporated isolator solution. Bromophenol Blue dye (0.05%) was loaded to every other well along with 8% sucrose and dried at room temperature, as a visual idicator of the isolator's ability to temporarily retard the dissolution of products within the isolator upon addition of the unpolymerized hydrogel. Visual comparison demonstrated that linear polyacrylamide had a slight advantage over the next best polymer, Dextran T500.

EXAMPLE 13

Multiple Primers Incorporated into Hydrogel Posts within a Hydrogel Post Array Inclusion of between 3 to 12 different sets of primers in individual posts comprising a hydrogel post array were successfully undertaken using an isolator comprised of 8% sucrose, 1% Dextran T500, 13 mM Tris-base, 0.05% NP-40, 0.05% Tween20 and 0.2 µM of each primer and BKV DNA (~3,000 molecules per post) or no DNA. The isolator mixture has a pH of 10.6, which advantageously inhibits primer annealing during the evaporation of the isolator, FIG. 2(a) and FIG. 2(b). Mould heights of 1.1 mm were used and following polymerization, FIG. 2(c) and FIG. 2(d), detachment from the mould, FIG. 2(e), immersion into oil.

Figure 11:
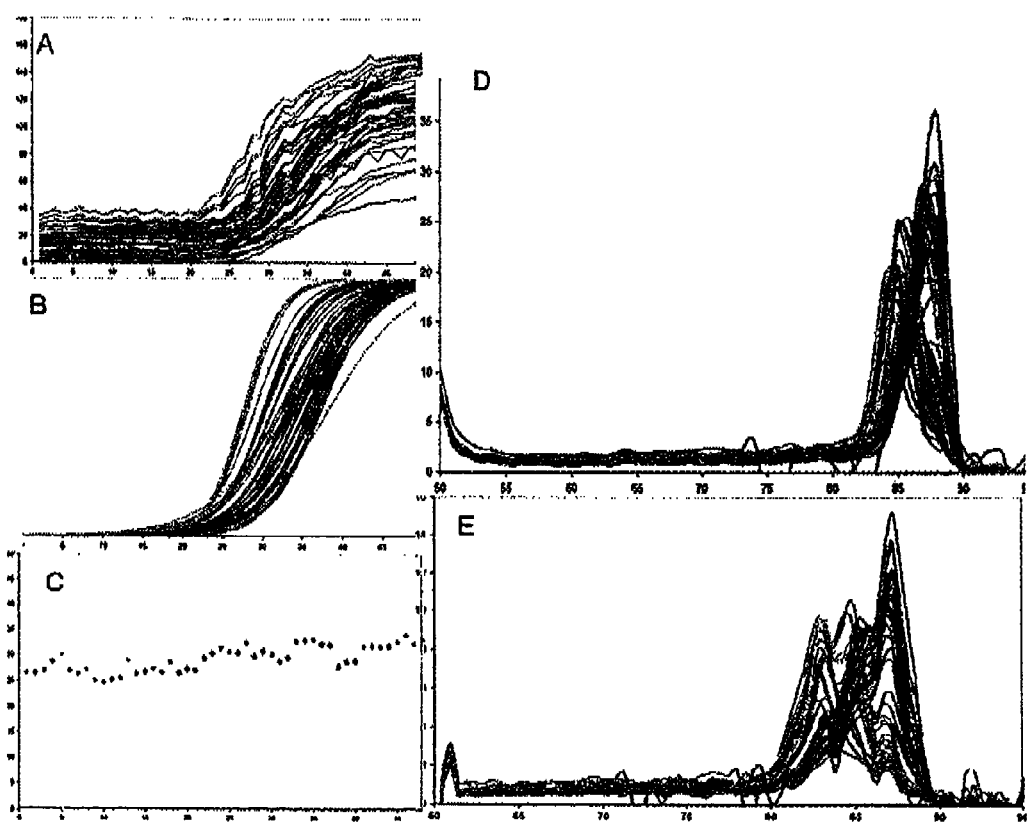
FIG. 11 shows PCR and MCA results of BKV DNA amplification with different product sizes for a multiple primer post array with (a) raw and (b) normalized PCR, (c) $C_P$ values and MCA charts with (d) 1° C. and (e) 0.25° C. resolution.

Twelve primer pairs were used spanning product sizes from 150 to 1000 b.p. in accordance with the primers listed in Table 1, using BKV as a template, and isolator deposited as described herein. Each pair was represented by four posts providing statistical value to the experiments and serving redundancy in case posts were disrupted during detachment of the mould. The mould was dried for an hour on open air and transferred to the gas chamber to be filled with PCR-polymerization mixture and photo-polymerized as described herein. The PCR and MCA were performed as described herein, and the images were processed in ImageJ and Microsoft Excel with the typical results shown in FIG. 11. In order to prove the size of amplified products the posts were detached from the glass support and placed on a vertical 8% polyacrylamide gel, polymerized in 0.5× TBE buffer (20 mM Tris-Borate, 0.5 mM EDTA). Electrophoresis extracted PCR products from the posts and separated them according to their sizes in the gel.

While particular embodiments of the present invention have been described in the foregoing, it is to be understood that other embodiments are possible within the scope of the invention and are intended to be included herein. It will be clear to any person skilled in the art that modifications of and adjustments to this invention, not shown, are possible without departing from the spirit of the invention as demonstrated through the exemplary embodiments. The invention is therefore to be considered limited solely by the scope of the appended claims.

What is claimed is:

1. A method for detecting a nucleic acid molecule within a hydrogel post array comprising a) Depositing on a substantially planar surface plural aqueous solutions each containing at least one nucleic acid capable of initiating an amplification of a selected template nucleic acid and a viscosity increasing solute, said plural aqueous solutions not being in fluid communication with each other and forming a multiplicity of deposits;

b) Allowing said aqueous solutions to evaporate in said deposits;

c) Establishing an array of hydrogel posts, each hydrogel post containing a cell-free, enzymatic, nucleic-acid amplification system, said hydrogel posts comprising the array being arranged so as any given post impinges upon only one deposit;

d) distributing on at least one of said hydrogel posts nucleic acid molecules, at least one of which comprises a template nucleic acid for said amplification system;

e) incubating said hydrogel posts under conditions promoting the synthesis of an amplified nucleic acid product by said amplification system from said at least one template;

wherein said amplification system comprises at least two non-immobilized nucleic acids capable of promoting synthesis of amplified nucleic acid product from said template.

2. The method of claim 1 wherein the viscosity increasing solute is selected from the group consisting of monosaccharide, disaccharide, polysaccharide, linear polyacrylamide, polyvinyl pyrrolidone, and polyethyleneglycol.

3. The method of claim 2 wherein the solute is a disaccharide selected from the group consisting of sucrose, maltose or trehalose.

* * * * *

SEQUENCE LISTING

<160> NUMBER OF SEQ ID NOS: 19

<210> SEQ ID NO 1
<211> LENGTH: 21
<212> TYPE: DNA
<213> ORGANISM: BK virus

<400> SEQUENCE: 1
aaacacccta acctcttcta c                                            21

<210> SEQ ID NO 2
<211> LENGTH: 20
<212> TYPE: DNA
<213> ORGANISM: BK virus

<400> SEQUENCE: 2
ttcctttttg ctaagtgacc                                              20

<210> SEQ ID NO 3
<211> LENGTH: 19
<212> TYPE: DNA
<213> ORGANISM: BK virus

<400> SEQUENCE: 3
tattttaaga tccgcctga                                               19

<210> SEQ ID NO 4
<211> LENGTH: 21
<212> TYPE: DNA
<213> ORGANISM: BK virus

<400> SEQUENCE: 4
gcctgtttac taacagctct g                                            21

<210> SEQ ID NO 5
<211> LENGTH: 21
<212> TYPE: DNA
<213> ORGANISM: BK virus

<400> SEQUENCE: 5
gcctctttgt aaagctgata g                                            21

<210> SEQ ID NO 6
<211> LENGTH: 20
<212> TYPE: DNA
<213> ORGANISM: BK virus

<400> SEQUENCE: 6
catgtgacca acacagctac                                              20

```
<210> SEQ ID NO 7
<211> LENGTH: 21
<212> TYPE: DNA
<213> ORGANISM: BK virus

<400> SEQUENCE: 7
ctaggtattt tgggactttc a                                                  21

<210> SEQ ID NO 8
<211> LENGTH: 19
<212> TYPE: DNA
<213> ORGANISM: BK virus

<400> SEQUENCE: 8
tgcttatcca gttgagtgc                                                     19

<210> SEQ ID NO 9
<211> LENGTH: 21
<212> TYPE: DNA
<213> ORGANISM: BK virus

<400> SEQUENCE: 9
ccagtcccag gtaatgaata c                                                  21

<210> SEQ ID NO 10
<211> LENGTH: 21
<212> TYPE: DNA
<213> ORGANISM: BK virus

<400> SEQUENCE: 10
gaattacagg tcaaagtacc c                                                  21

<210> SEQ ID NO 11
<211> LENGTH: 18
<212> TYPE: DNA
<213> ORGANISM: BK virus

<400> SEQUENCE: 11
gtgcatgagc atggtgga                                                      18

<210> SEQ ID NO 12
<211> LENGTH: 21
<212> TYPE: DNA
<213> ORGANISM: BK virus

<400> SEQUENCE: 12
aagctaagtg ctgaaaatga c                                                  21

<210> SEQ ID NO 13
<211> LENGTH: 18
<212> TYPE: DNA
<213> ORGANISM: BK virus

<400> SEQUENCE: 13
cccaaccaaa agaaaagg                                                      18

<210> SEQ ID NO 14
<211> LENGTH: 16
<212> TYPE: DNA
<213> ORGANISM: Homo sapiens

<400> SEQUENCE: 14
cacagcgagg tgagcc                                                        16
```

```
<210> SEQ ID NO 15
<211> LENGTH: 18
<212> TYPE: DNA
<213> ORGANISM: Homo sapiens

<400> SEQUENCE: 15
ctcctgtctt acaggccc                                                  18

<210> SEQ ID NO 16
<211> LENGTH: 26
<212> TYPE: DNA
<213> ORGANISM: Homo sapiens

<400> SEQUENCE: 16
cagaagtttt tgagagtggc atgatg                                         26

<210> SEQ ID NO 17
<211> LENGTH: 28
<212> TYPE: DNA
<213> ORGANISM: Homo sapiens

<400> SEQUENCE: 17
gctgacttct atttatataa cttcaagc                                       28

<210> SEQ ID NO 18
<211> LENGTH: 20
<212> TYPE: DNA
<213> ORGANISM: Herpes Simplex Virus 1

<400> SEQUENCE: 18
cgccggcgga tacgaagacg                                                20

<210> SEQ ID NO 19
<211> LENGTH: 20
<212> TYPE: DNA
<213> ORGANISM: Herpes Simplex Virus 1

<400> SEQUENCE: 19
cgtcgcgggt tggccacata                                                20
```